United States Patent
Hamdi et al.

(10) Patent No.: US 6,632,798 B2
(45) Date of Patent: Oct. 14, 2003

(54) METHODS FOR INHIBITING ANGIOGENESIS

(75) Inventors: Hamdi K. Hamdi, Los Angeles, CA (US); Jeffrey H. Tavis, Lomita, CA (US); Raquel Castellon, Norwalk, CA (US)

(73) Assignee: Antigen Biologicals Corporation, Los Angeles, CA (US)

( * ) Notice: Subject to any disclaimer, the term of this patent is extended or adjusted under 35 U.S.C. 154(b) by 0 days.

(21) Appl. No.: 10/153,003

(22) Filed: May 22, 2002

(65) Prior Publication Data

US 2003/0004117 A1 Jan. 2, 2003

Related U.S. Application Data

(60) Provisional application No. 60/292,947, filed on May 23, 2001.

(51) Int. Cl.[7] .......................... A61K 31/70; A61K 31/35
(52) U.S. Cl. ......................................... 514/27; 514/460
(58) Field of Search .................................. 514/27, 460

(56) References Cited

U.S. PATENT DOCUMENTS

| | | | | |
|---|---|---|---|---|
| 6,117,844 A | * | 9/2000 | Fredrickson | 514/27 |
| 6,361,803 B1 | * | 3/2002 | Cuomo et al. | 424/725 |
| 6,437,004 B1 | * | 8/2002 | Perricone | 514/738 |
| 6,440,465 B1 | * | 8/2002 | Meisner | 424/725 |
| 2002/0004077 A1 | * | 1/2002 | Cuomo et al. | 424/725 |

OTHER PUBLICATIONS

McCarty, Med. Hypothesis, vol. 50(6), pp. 511–514 (abstract), Jun. 1998.*

Visioli et al, Biochem. Biophys. Res. Commun., vol. 247(1), pp. 60–64 (abstract), Jun. 1998.* de la Puerta et al, Biochem. Pharmacol., vol. 57(4), pp. 445–449 (abstract), Feb. 1999.*

Park et al, Chem Pharm Bull (tokyo), vol. 47(7), pp. 1029–1031 (abstract), Jul. 1999.*

* cited by examiner

*Primary Examiner*—James H Reamer
(74) *Attorney, Agent, or Firm*—Stetina Brunda Garred & Brucker

(57) ABSTRACT

Methods for inhibiting angiogenisis are disclosed the comprise administering oleouropein and/or the products of its hydrolysis in therapeutically effective amounts. The methods and compositions of the present invention are particularly effective in inhibiting the vascularization of endothelial cells, and may be utilized to treat a wide variety of cancers, ocular diseases, and inflammatory conditions.

30 Claims, 9 Drawing Sheets

Graph 1
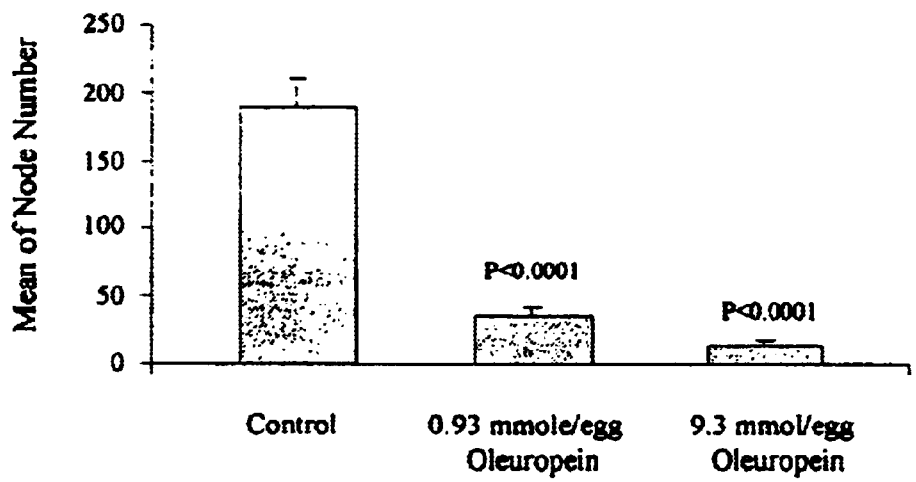
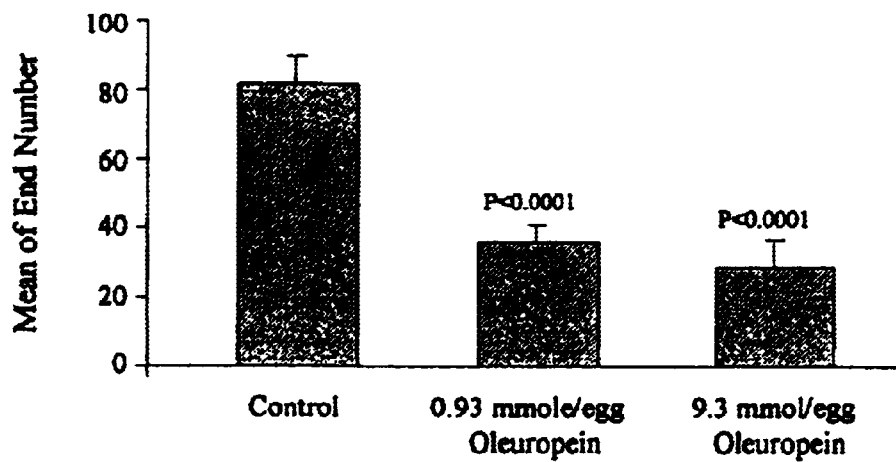

(Oleuropein treated CAM-9.3μmole/egg)

(Oleuropein treated CAM-0.93µmole/egg)

Figure 3
(Control CAM)
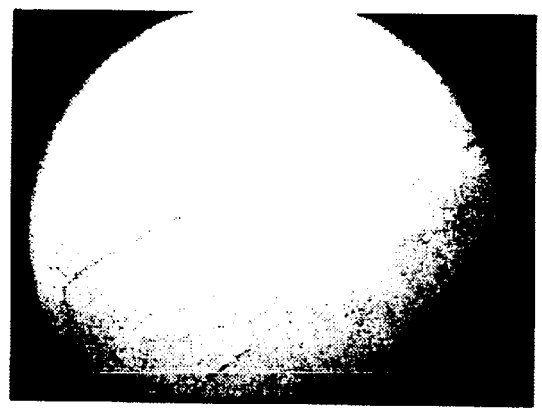
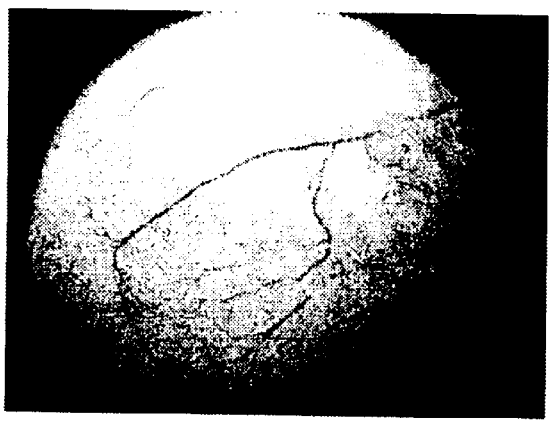

(Control and olive leaf extract treated CAMs)

Mouse ear model

METHODS FOR INHIBITING ANGIOGENESIS

CROSS-REFERENCE TO RELATED APPLICATIONS

The present application is a non-provisional application claiming priority to U.S. Provisional Patent Application Ser. No. 60/292,947, entitled Compound and Method for Inhibiting Angiogenesis, Filed May 23, 2001.

STATEMENT RE: FEDERALLY SPONSORED RESEARCH/DEVELOPMENT (Not Applicable)

BACKGROUND OF THE INVENTION

The present invention reports a method for efficiently inhibiting angiogenesis and regressing existing blood vessels. More particularly, this invention relates to methods of treating diseases associated with pathogenic angiogenesis and to delivering anti-angiogenic activity in live animals including humans having such diseases.

Angiogenesis is the growth of new blood vessels from previously existing microvessels. The angiogenic process is a natural and regulated process in wound healing, fetal and embryonal development and in the formation of the corpus luteum, endometrium and placenta. These processes are vital to health and growth and are very well regulated by angiogenic promoters and inhibitors. In disease states, however, this regulation can be circumvented and lead to pathogenic angiogenesis. Pathogenic angiogenesis is unwanted angiogenesis and is the target for therapeutic interventions. A number of human diseases are characterized by unwanted angiogenesis. These include cancer, diabetic retinopathy, age-related macular degeneration, the formation of the arthritic panus and in psoriasis.

In cancer, for example, angiogenesis plays a critical role in the survival and metastasis of tumors. Tumors secrete angiogenic factors that promote the division and migration of endothelial cells, which begins the angiogenic process. It has become clear that tumors need to be vascularised to grow and metastasize. If a tumor's blood supply is curtailed, the tumor will not grow beyond 0.4 mm. Tumor cells, absent an adequate blood supply, ultimately become necrotic and/or apoptotic. Thus blood vasculature and especially new blood vessel growth or angiogenesis is an important aspect of tumor biology. Therapies directed against angiogenesis could lead to the abrogation or alleviation of these diseases.

The pathogenesis and blindness associated with ocular diseases such as diabetic retinopathy and age-related macular degeneration is a direct outcome of unwanted angiogenesis. In ocular tissue, angiogenesis is the most common cause of blindness. Proliferative diabetic retinopathy is characterized by retinal blood vessel incursion of the vitrous. Age-related macular degeneration is a disease of the macula and is distinguished from the dry form by choroidal blood vessel ingrowth penetrating bruchs membrane. Angiogenic pathology is also associated with retinopathy of prematurity, corneal graft rejection, neovascular glaucoma and retrolental fibroplasia. Diseases associated with retinal/choroidal neovascularization include, but are not limited to, diabetic retinopathy, macular degeneration, sickle cell anemia, sarcoid, syphilis, pseudoxanthoma elasticum and Paget's disease.

BRIEF SUMMARY OF THE INVENTION

In one feature, this invention relates to a method of inhibiting the vascularization of endothelial cells, the method comprising contacting a cell, tissue or organ which has endothelial cells with an anti-angiogenic amount of a compound of Formula I. Compounds of Formula I have the following general formula:

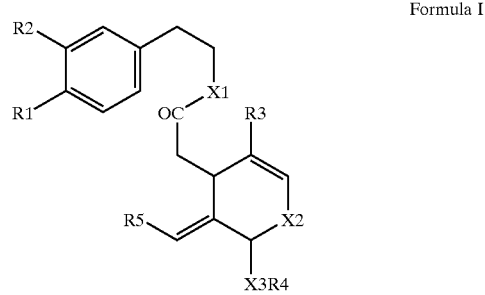

Formula I

In formula I, R1 and R2 are functional groups including, but not limited to, hydroxyi.

In formula I, R3 is a functional group including, but not limited to, hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $COOCH_3$.

In formula I, R4 is a functional group including but not limited to, hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen, $NO_2$, $NH_3$, carbohydrate, amino acid, nucleotide and lipid.

In formula I, R5 is a functional group including but not limited to, hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $CH_3$.

In formula I, X1–X3, are functional groups including, but not limited to, oxygen, sulfur, $CH_2$-, or carboxy, which can be different but preferably are identical functional groups.

In a preferred embodiment of the invention, the compound of formula I is Oleuropein with formula $C_{25}H_{32}O_{13}$, as described in the tenth edition of THE MERK INDEX with monograph number 6709, and shown in Formula II.

Formula II

Plant extract x, which can comprise any of the ethanolic, acetone, inorganic and organic acid or base and/or aqueous extraction of plant extract x contains: Oleuropein, the compound shown in formula II. Plant extract x is derived from plants including but not limited to the leaves, buds, fruit, wood, bark and roots of the olive tree *Olea europaea* L., the privet tree, *Ligustrum obtusifolium* (Oleaceae), etc.

In another aspect, this invention relates to a method for potently inhibiting unwanted angiogenesis in a tissue or organ, the method comprising contacting the cell with a an ethanolic, acetone, inorganic and organic acid or base and/or aqueous solution of plant extract x. or a derivative of the ethanolic, acetone, inorganic and organic acid or base and/or aqueous solution or a component thereof, containing Oleouropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, in an amount sufficient to inhibit angiogenesis. In a presently preferred embodiment, the cell is in a live organism.

In yet another aspect, this invention relates to a method of treating angiogenic-related diseases mediated by or associated with undesired and uncontrolled angiogenesis, the method comprising administering to a live animal an anti-angiogenic compound of the ethanolic, acetone, inorganic and organic acid or base and/or aqueous solution of extract X or a derivative of the ethanolic, acetone, inorganic and organic acid or base and/or aqueous or a component thereof, containing Oleouropein, the compound shown in formula II or a derivative thereof as shown in formula I or products of its hydrolysis, which include but are not limited to oleuropein aglycone, elenolic acid, beta-3,4-dihydroxyphenyethyl alcohol and methyl-o-methyl elenolate or a pharmaceutical composition thereof, solution in a dosage sufficient to inhibit angiogenesis. These methods are useful for ameliorating the effects of conditions that are characterized by abnormal or undesirable angiogenesis or endothelial cell proliferation and/or migration.

Other features, objects and advantages of the invention and its preferred embodiments will become apparent from the detailed description which follows.

BRIEF DESCRIPTION OF THE DRAWINGS

These as well as other features of the present invention will become more apparent upon reference to the drawings wherein:

Graph 1A. Graph of the inhibition of blood vessel growth by Oleuropein based on node number of blood vessels in the chick chorioallantoic membrane (CAM). Bar graphs represent the mean and standard error values. Statistical significance was obtained using an unpaired t test.

Graph 1B. Graph of the inhibition of blood vessel growth by Oleuropein based on end number of blood vessels in the CAM. Bar graphs represent the mean and standard error values. Statistical significance was obtained using an unpaired t test.

Figure 1:
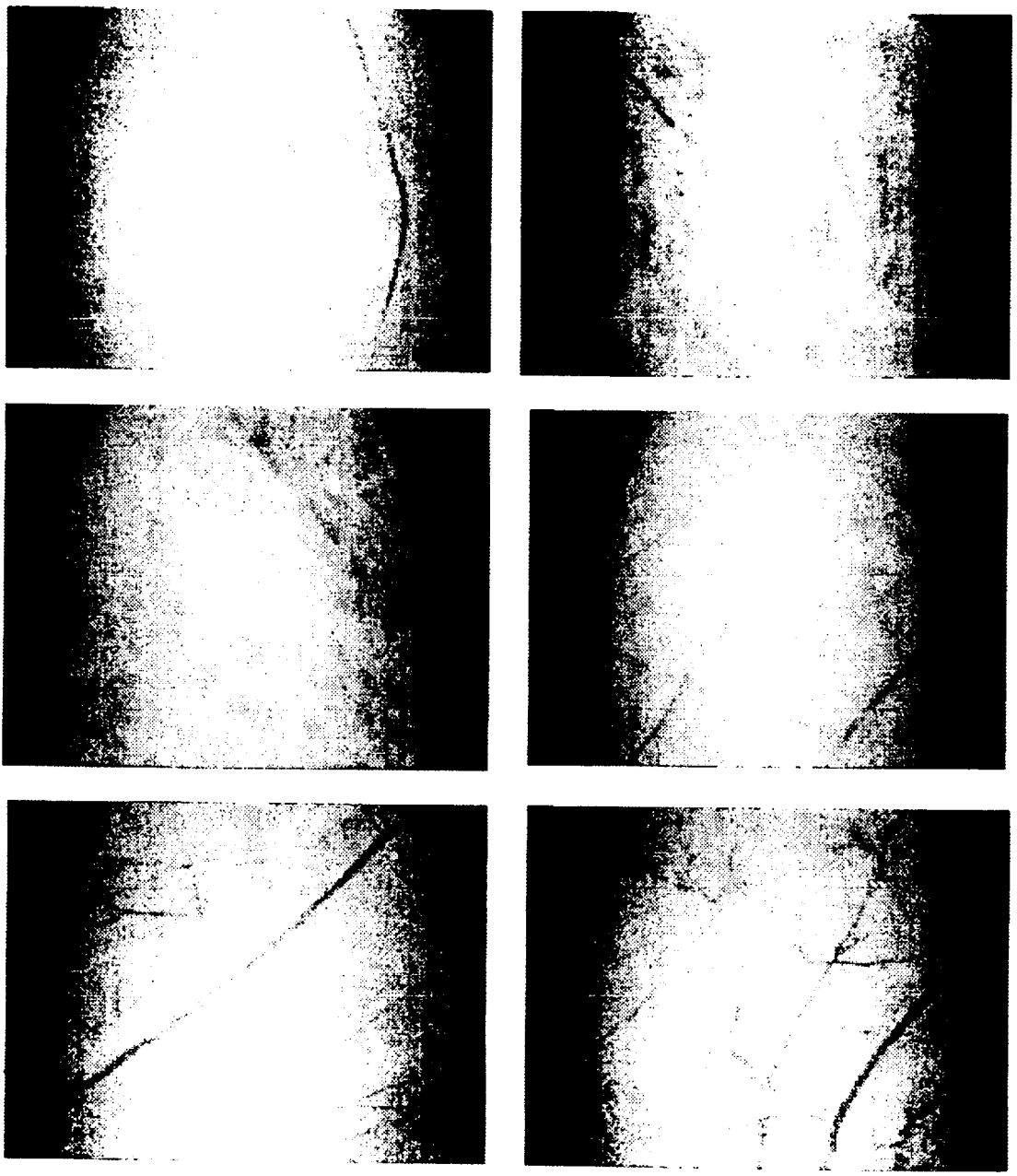

FIG. 1. Representative photographs illustrating the inhibition of angiogenesis by an aqueous solution of Oleuropein. Three-day-old chick embryos were injected with 0.5 cc containing 9.3 μmol/egg of Oleuropein. The injections were made directly into the yolk sac. The embryos were incubated for 4 days post injection. The egg was cracked and the CAM was photographed using a Kodak mds 100 camera.

Figure 2:
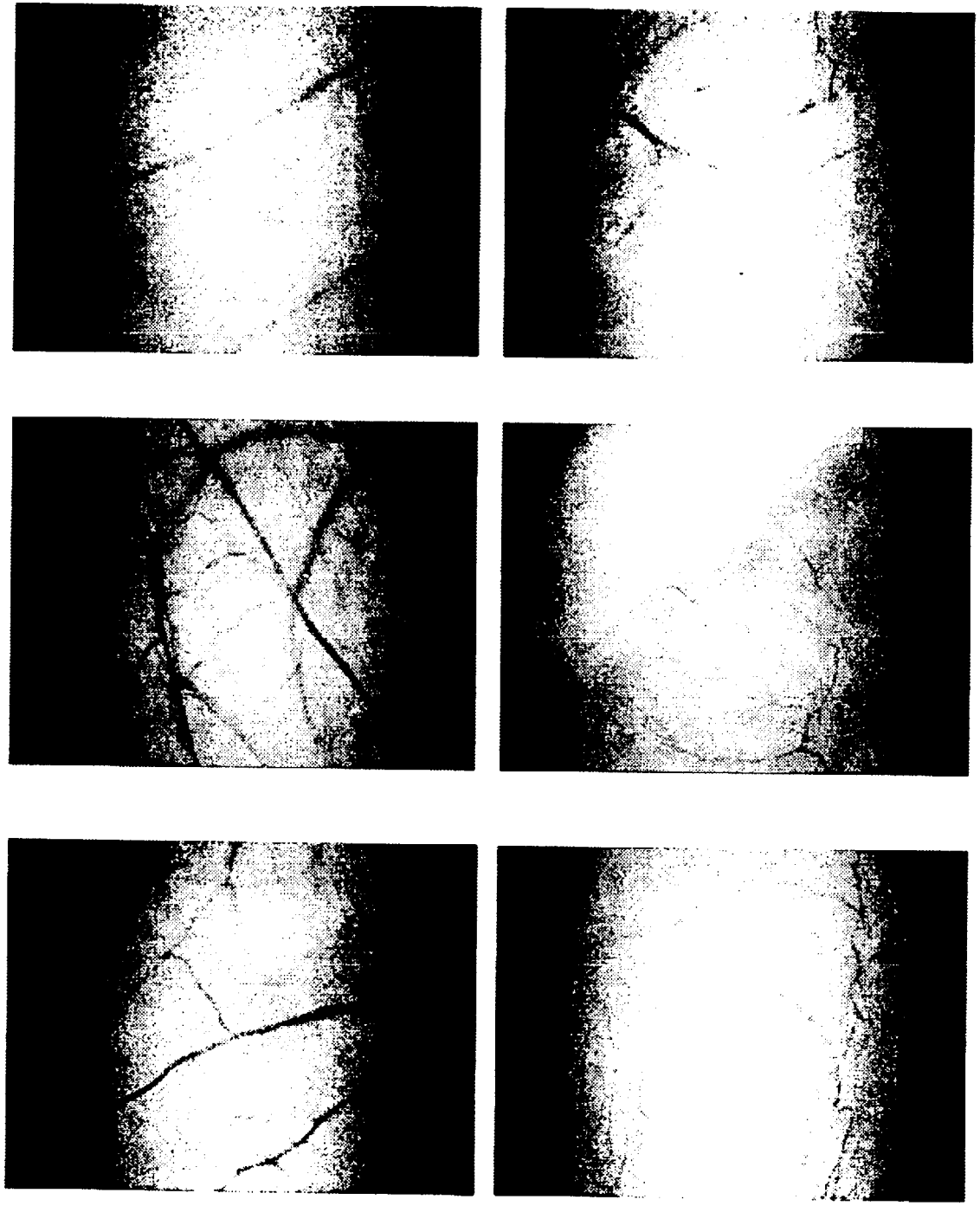

FIG. 2. Representative photographs illustrating the inhibition of angiogenesis by an aqueous solution of Oleuropein. Three-day-old chick embryos were injected with 0.5 cc of a 0.93 μmol/egg of Oleuropein. The injections were made directly into the yolk sac. The embryos were incubated for 4 days post injection. The egg was cracked and the CAM was photographed using a Kodak mds 100 camera.

FIG. 3. Representative photographs illustrating the level of angiogenesis in the control. The effects of an aqueous solution on angiogenesis. Three-day-old chick embryos were injected with 0.5 cc of distilled water. The injections were made directly into the yolk sac. The embryos were incubated for 4 days post injection. The egg was cracked and the CAM was photographed using a Kodak mds 100 camera.

Figure 4:
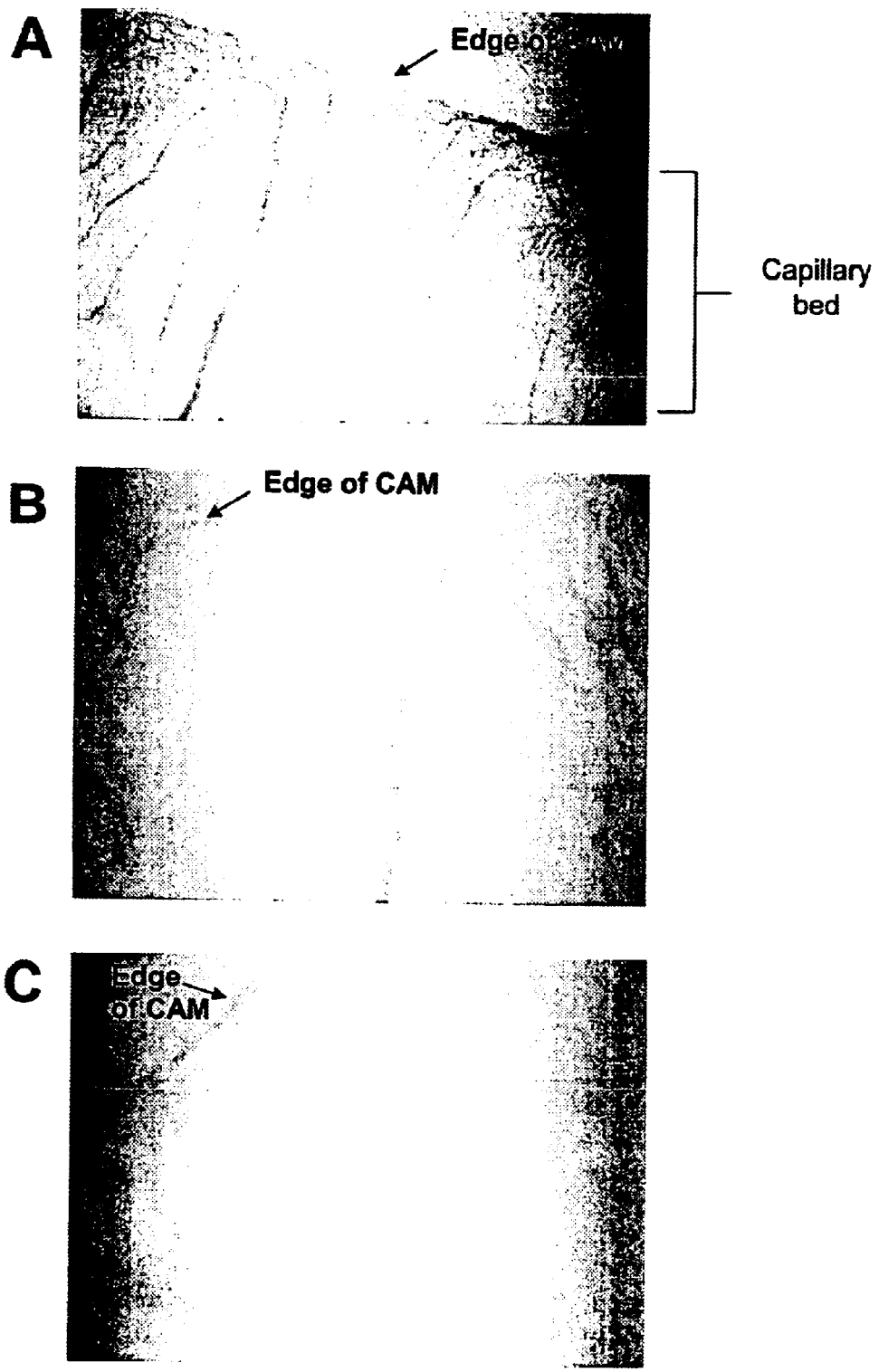

FIG. 4. Compares the capillary beds of control and experimental CAMs. Shows the disappearance of capillaries in the Oleuropein treated eggs.

Figure 5:

FIG. 5. A whole embryo mount including CAM. Illustrates the effect of Oleuropein on the size of the CAM and subsequently on the size of the embryo.

Figure 6:
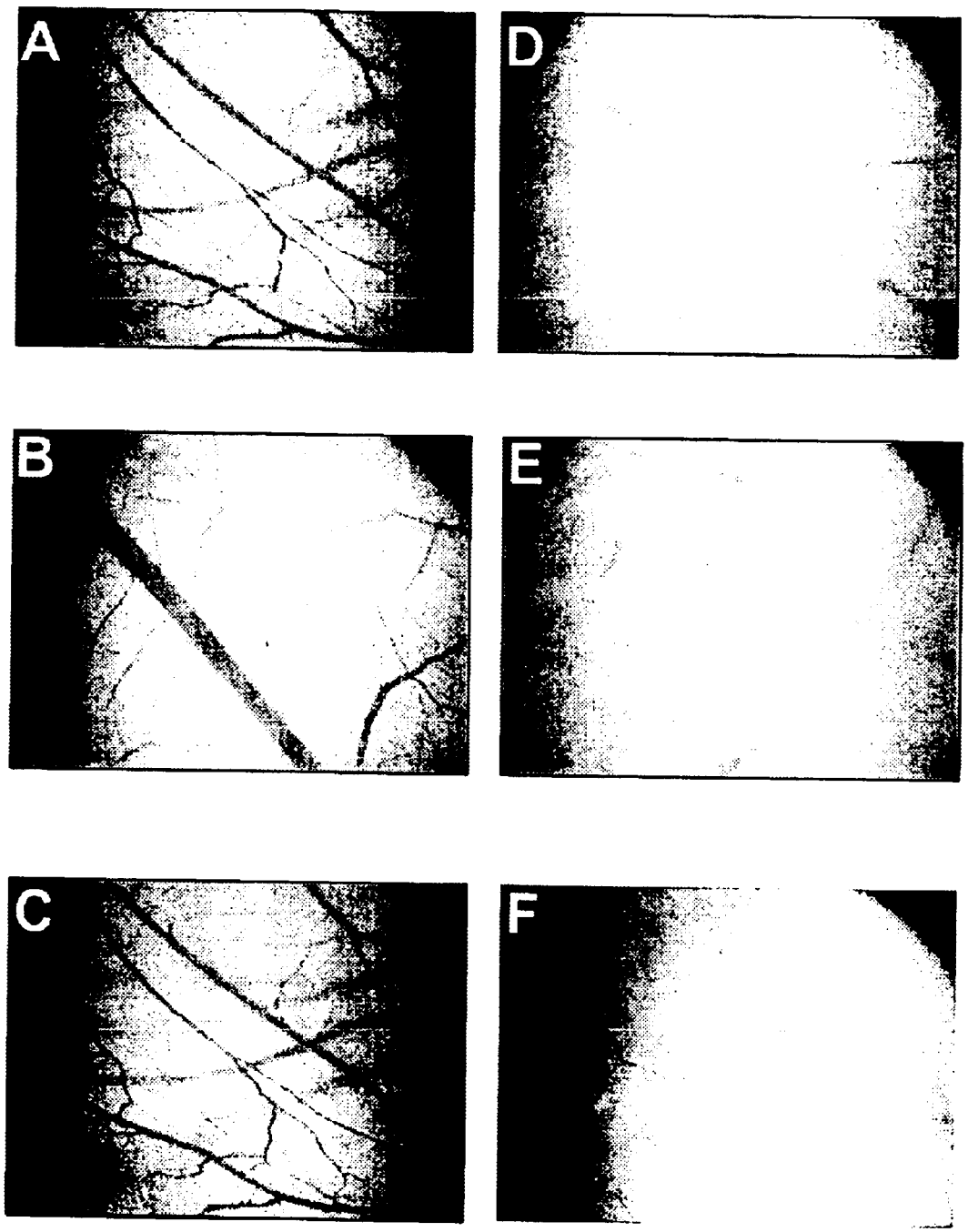

FIG. 6. Representative photographs illustrating the inhibition of angiogenesis by an aqueous solution of olive leaf extract. Photographs (A), (B), and (C) represent CAMs of control embryos injected with water/saline. Photographs (D), (E), and (F) represent chick embryos that were injected with 0.5 cc of olive leaf extract. The injections were made directly into the yolk sac. The embryos were incubated for 4 days post injection. The eggs were cracked and the CAM was photographed using a Kodak mds 100 camera.

Figure 7:
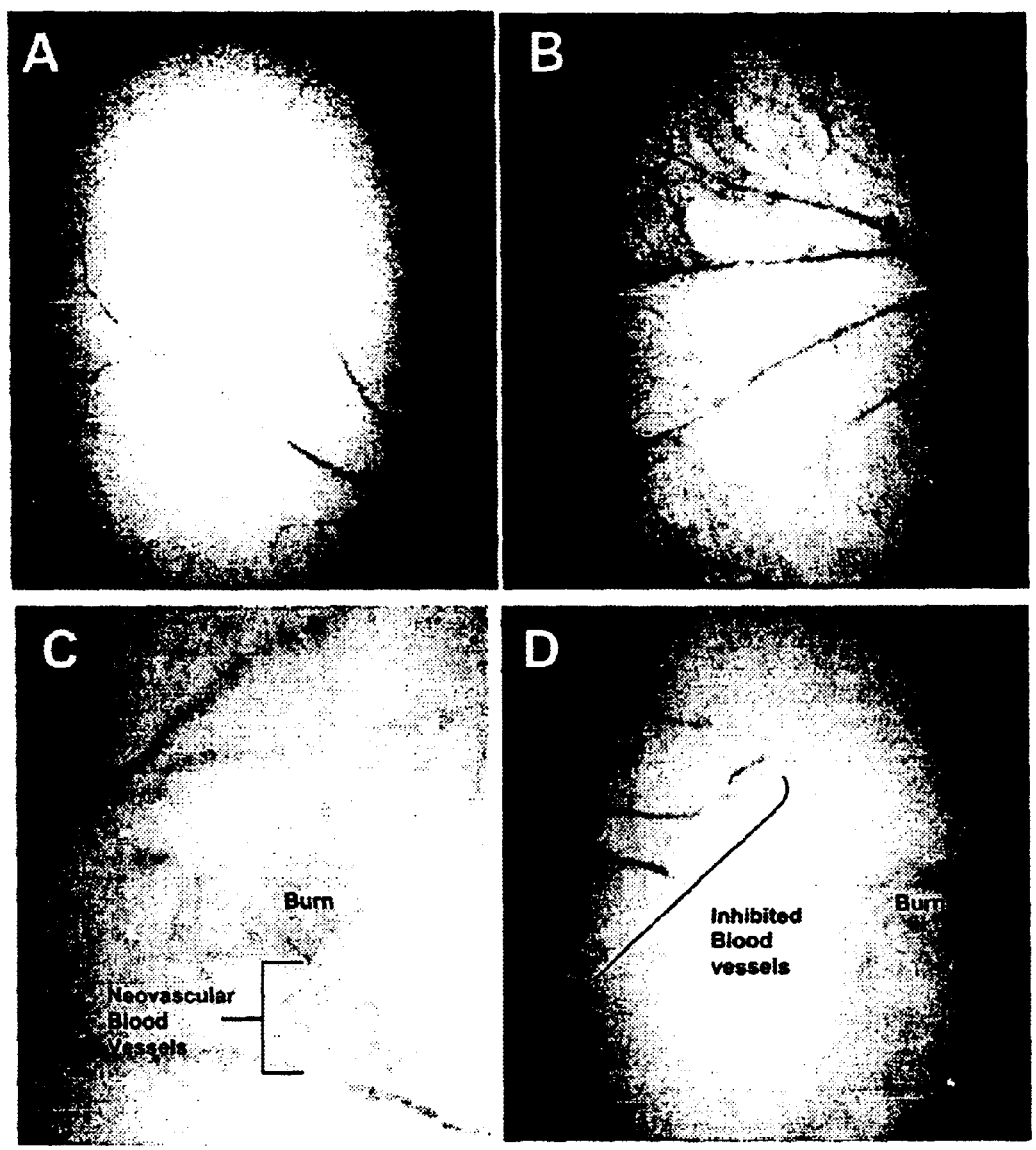

FIG. 7. Comparative photographs illustrating the inhibition of angiogenesis by an aqueous solution of Oleuropein. Photograph (A) displays an adult mouse ear that has not been burned or treated in any way. The vascularization represents what is normally found in the adult mouse ear. Photograph (B) represents induction of blood vessel growth by a sodium hydroxide burn. A very significant angiogenic response was produced in comparison to the unburned ear. Photograph (C) shows a more detailed angiogenic response engulfing the burn area. Blood vessels can be seen sprouting from existing ones and traveling towards the burn. Photograph (D) shows a mouse ear that has been burned but new blood vessel growth has been inhibited by intraperitoneal injections of Oleuropein.

Figure 8:
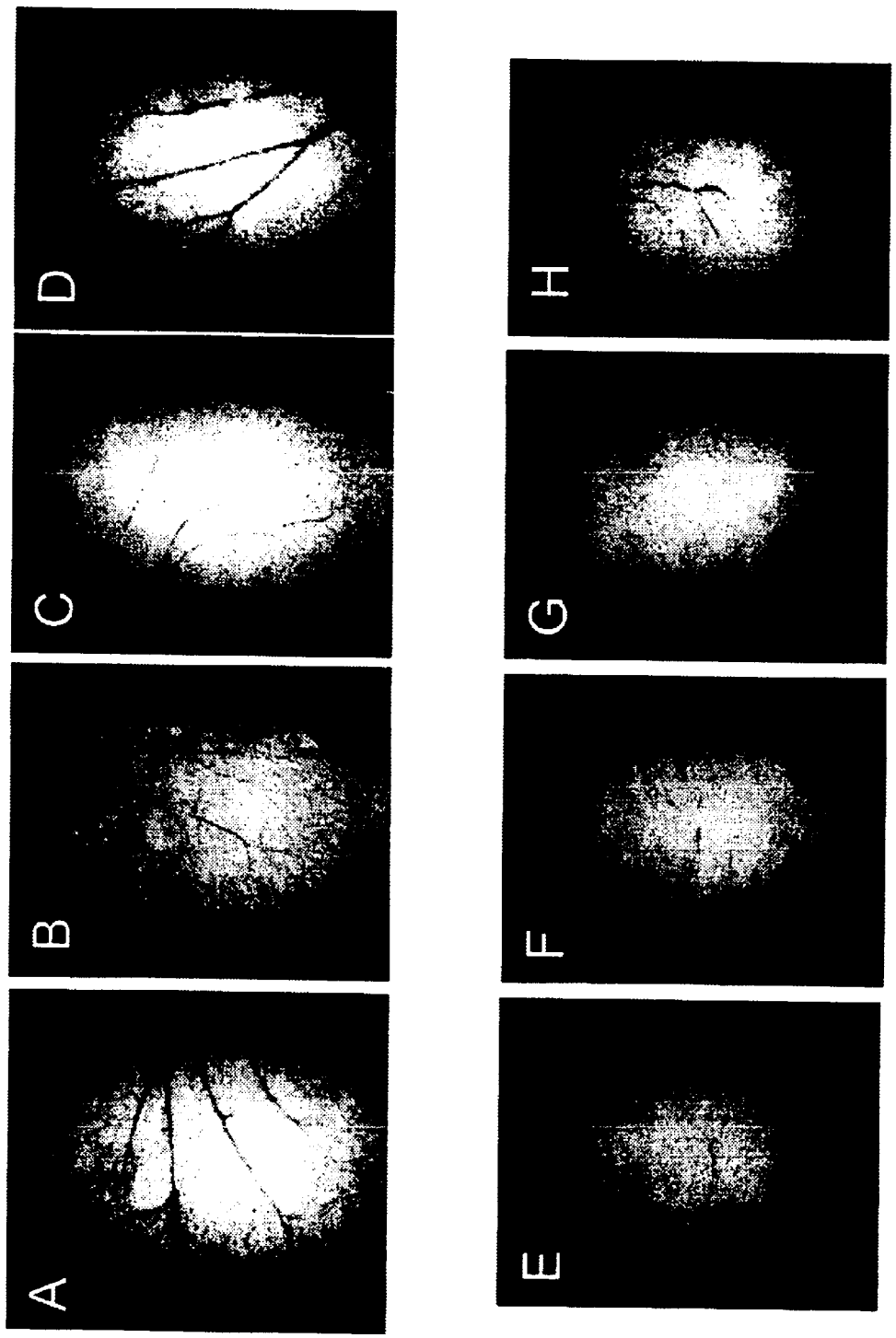

FIG. 8. Comparative photographs illustrating the inhibition of angiogenesis by an aqueous solution of Oleuropein. Photographs (A), (B), (C), and (D) display adult mouse ears that have been burned by sodium hydroxide as described below. The vascularization represents induction of blood vessel growth by the sodium hydroxide burn. A very significant angiogenic response was produced in comparison to the unburned ear. Photographs (E), (F), (G), and (H) show mouse ears that have been burned by sodium hydroxide, but mice were treated with Oleuropein. Blood vessel growth was potently inhibited by the Oleuropein treatments.

DETAILED DESCRIPTION OF THE INVENTION

The detailed description set forth below is intended as a description of the presently preferred embodiment of the invention, and is not intended to represent the only form in which the present invention may be practiced or utilized. The description sets forth the functions and sequences of steps for practicing the invention. It is to be understood, however, that the same or equivalent functions and sequences may be accomplished by different embodiments and that the equivalent functions and sequences are also intended to be encompassed within the scope of the invention.

A. Definitions

The term "animal" refers to an organism with a closed circulatory system of blood vessels and includes birds, mammals and crocodiles. The term "animal" used here also includes human subjects.

The term "angiogenesis" refers to the generation of new blood vessels into cells, tissue, organs or tumors.

The term "metastasis" refers to the process by which tumor cells are spread to distant parts of the body. The term is also used herein to refer to a tumor that develops through the metastatic process.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, topical and inhalation routes as described herein.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

"An amount sufficient," "an effective amount," "therapeutically effective amount" or "anti-angeogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularization of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigor or vitality or decreased pain as subjective symptoms of improvement or response to therapy. Alternatively, the clinician may notice decrease in tumor size or tumor burden based on physical exam, laboratory parameters, tumor markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation such as subjective symptoms or objective signs as discussed above.

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamine, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "S-alkyl" is used herein to refer to the group —SR, where R is lower alkyl or substituted lower alkyl as defined herein.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

"Substituted aryl" refers to aryl as just described including one or more functional groups such as lower alkyl, acyl, halogen, alkylhalos (e.g. $CF_3$), hydroxy, amino, alkoxy, alkylamine, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "halogen" is used herein to refer to fluorine, bromine, chlorine and iodine atoms.

The term "hydroxy" is used herein to refer to the group —OH.

The term "amino" is used to refer to the group —NRR', where R and R' may independently be hydrogen, alkyl, substituted alkyl, aryl, substituted aryl or acyl.

The term "nitro" is used herein to refer to the group -$NO_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkenyl" is used herein to refer to an unsaturated branched, straight chain or cyclic monovalent hydrocarbon radical having at least one carbon-carbon double bonds. The radical can be in either the cis or trans conformation about the double bond(s). Suitable alkenyl radicals include, for example, ethenyl, propenyl, isopropenyl, cyclopropenyl, butenyl, isobutenyl, cyclobutenyl, tert-butenyl, pentenyl, hexenyl, etc.

The term "alkynyl" is used herein to refer to an unsaturated branched, straight chain or cyclic monovalent hydrocarbon radical having at least one carbon-carbon triple bond. Suitable alkynyl radicals include, for example, ethynyl, propynyl, butynyl, isobutynyl, pentynyl, hexynyl, etc.

B. Compounds

The present invention relates to the discovery that compounds of formula I inhibit angiogenesis and are useful for treating angiogenic diseases. Compounds of Formula I have the following general formula:

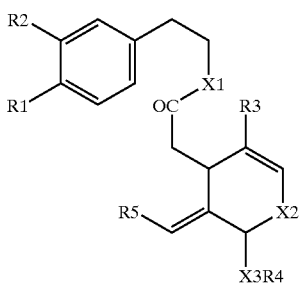

Formula I

Wherein RI, R2, R3, R4, R5, and X1, X2, and X3 are as defined above. In a preferred embodiment of the invention, the compound of formula I is Oleuropein as shown below in Formula II:

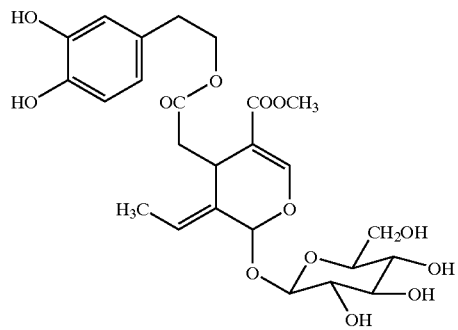

Formula II

Oleuropein, the compound used in the present invention can be readily obtained from plants including but not limited to the olive tree *Olea europaea* L. and the privet tree, *Ligustrum obtusifolium* (Oleaceae).

Compounds suitable for use in the methods of the present invention can readily be identified using in vitro and in vivo screening assays. Such assays may screen for the ability of a particular compound to inhibit angiogenesis or the vascularization of endothelial cells in vitro and in vivo. For instance, the chick embryo chorioallantoic membrane (CAM) assay, which is described in more detail below, can be used to screen a given compound for its ability to inhibit vascularization. In the chorioallantoic membrane assay as performed in this invention, fertilized chick embryos are injected with a compound on day 3 or 4. The embryos are then allowed to develop for 4 days post injection upon which the shell is cracked and the chorioallantoic membrane is photographed. Based on the number of blood vessel nodes and ends present in the CAM the complexity of vascularization can be assessed. This assay can be used to assess the anti-angeogenic properties of the compounds in this invention. It will be readily apparent to those skilled in the art that the compounds in this invention can be administered alone, in the form of a pharmaceutically acceptable salt and/or in the form of a pharmaceutical composition.

C. Uses for the Compounds of the Present Invention

As explained above, the present invention relates to the discovery that the compounds of formula I or its preferred embodiment Oleuropein, or it hydrolysis products are useful for inhibiting angiogenesis and, in turn, for treating diseases associated with unwanted angiogenesis. As such, in one embodiment, the present invention provides a method of inhibiting unwanted angiogenesis in a cell, the method comprising contacting the cell with an effective amount, i.e., an anti-angiogenic amount, of a compound of formula I or it preferred embodiment Oleuropein or its hydrolysis products or its hydrolysis products. In another embodiment, the present invention provides a method of inhibiting the vascularization of endothelial cells, the method comprising contacting a cell, tissue or organ containing the endothelial cells with an effective amount of a compound of formula I or its preferred embodiment Oleuropein or its hydrolysis products. In a presently preferred embodiment, the cells are in an animal subject.

This invention relates to a method of treating diseases associated with undesired and uncontrolled angiogenesis, the method comprising administering to an animal an anti-angiogenic compound of formula I or its preferred embodiment Oleuropein or its hydrolysis products in an amount, i.e., a dosage, sufficient to inhibit angiogenesis. The particular dosage of a compound of formula I or its preferred embodiment Oleuropein or its hydrolysis products required to inhibit angiogenesis and/or angiogenic diseases will depend upon the severity of the condition, the route of administration, and related factors that will be decided by the attending physician. Generally, accepted and effective daily doses will be the amount sufficient to effectively inhibit angiogenesis and/or angiogenic diseases.

The methods of treatment provided by this invention are practiced by administering to an animal in need thereof a dose of a compound of formula I or its preferred embodiment Oleuropein or its hydrolysis products (or a pharmaceutically acceptable salt or solvate thereof) that is effective to inhibit angiogenesis and/or angiogenic diseases. The term "inhibit" is used herein to include its generally accepted meaning which includes prophylactically treating a human subject to incurring angiogenesis and/or angiogenic diseases, and holding in check and/or treating existing angiogenesis and/or angiogenic diseases. As such, the present invention includes both medical therapeutic and/or prophylactic treatment, as appropriate.

The methods of the present invention can be used to treat a wide variety of diseases. Diseases associated with corneal neovascularization that can be treated using the methods of the present invention include, but are not limited to, diabetic retinopathy, retinopathy of prematurity, corneal graft rejection, neovascular glaucoma and retrolental fibroplasia, epidemic keratoconjunctivitis, vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, rheumatoid arthritis, systemic lupus, polyarteritis, Wegeners sarcoidosis, Scleritis, Steven's Johnson disease, periphigoid radial keratotomy, and corneal graph rejection.

Diseases associated with retinal/choroidal neovascularization that can be treated using the methods of the present invention include, but are not limited to, diabetic retinopathy, macular degeneration, sickle cell anemia, sarcoid, syphilis, pseudoxanthoma elasticurn, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue, including all forms of proliferative vitreoretinopathy, whether or not associated with diabetes.

Diseases associated with chronic inflammation can also be treated using the methods of the present invention. Diseases with symptoms of chronic inflammation include, but are not limited to, inflammatory bowel diseases, such as Crohn's disease and ulcerative colitis, psoriasis, sarcoidosis and rheumatoid arthritis. Unwanted or uncontrolled angiogenesis is an important feature that these chronic inflammatory diseases all have in common. The chronic inflammation depends on continuous formation of capillary sprouts to maintain an influx of inflammatory cells. The influx and presence of the inflammatory cells produce granulomas, maintaining the chronic inflammatory state. Inhibition of angiogenesis using the compositions and methods of the present invention prevents the formation of the granulomas, thereby alleviating the disease.

As mentioned above, the methods of the present invention can be used to treat patients with inflammatory bowel diseases, such as Crohn's disease and ulcerative colitis. Crohn's disease occurs as a chronic transmural inflammatory disease that most commonly affects the distal ileum and colon, but may also occur in any part of the gastrointestinal tract from the mouth to the anus and perianal area. Patients with Crohn's disease generally have chronic diarrhea associated with abdominal pain, fever, anorexia, weight loss and abdominal swelling. Prevention of angiogenesis by the compositions and methods of the present invention inhibits the formation of the sprouts and prevents the formation of granulomas. Ulcerative colitis is also a chronic, nonspecific, inflammatory and ulcerative disease appearing in the colonic mucosa and is characterized by the presence of bloody diarrhea.

The inflammatory bowel diseases also affect the skin. Skin lesions are characterized by inflammation and angiogenesis and can occur at many sites other than in the gastrointestinal tract. The compositions and methods of the present invention can also be used to treat these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease can form anywhere in the body and, thus, the symptoms depend on the site of the granulomas and whether the disease active. The granulomas are created by the angiogenic capillary sprouts providing a constant supply of inflammatory cells. The compounds and method of this invention can be used to treat sarcoidosis.

The methods of the present invention can also be used to treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated using the methods of the present invention is rheumatoid arthritis. Rheumatoid arthritis is a chronic inflammatory disease characterized by nonspecific inflammation of the peripheral joints. It is thought that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Other diseases that can be treated using the methods of the present invention are hemangiomas, Osler-Weber-Rendu disease, or hereditary hemorrhagic telangiectasia, solid or blood borne tumors and acquired immune deficiency syndrome.

The methods of this invention are also effective in inhibiting angiogenesis associated with malignant tumor growth. This includes cancerous tumor growth on cells tissues and organs. The methods of the present invention are useful in treating the growth of a number of tumor cells and for treating a wide variety of cancers. Such tumor cells include, by way of example and not limitation, lung, colon, breast, ovarian, prostate and hepatic tumor cells as well as squamous cell carcinomas. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas.

In a particularly preferred embodiment, the present invention relates to methods of administering compounds of formula I or its preferred embodiment Oleuropein in combination with active immunotherapy (e.g., tumor vaccination).

Moreover, in accordance with the above methods, mammalian subjects include, but are not limited to, humans, laboratory animals, domestic pets and farm animals.

D. Pharmaceutical Formulations/Routes of Administration

In the methods of the present invention, the compounds of formula I or its preferred embodiment Oleuropein or its hydrolysis products can be delivered or administered to a mammal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to depress, suppress or inhibit angiogenesis or result in amelioration of symptoms associated with angiogenic diseases.

The compounds of formula I or its preferred embodiment Oleuropein or its hydrolysis products, which are used in the methods of the present invention, can be incorporated into a variety of formulations for therapeutic administration. More particularly, compounds of formula I or its preferred embodiment Oleuropein or its hydrolysis products can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

In addition, the compounds of formula I or its preferred embodiment Oleuropein or its hydrolysis products can be formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

Compounds of formula I or its preferred embodiment Oleuropein or its hydrolysis products can be administered alone, in combination with each other, or they can be used in combination with other known compounds (e.g., other anti-cancer drugs or other drugs, such as AZT, anti-inflammatories, antibiotics, corticosteroids, vitamins, etc.). For instance, the compound of formula I or its preferred embodiment Oleuropein or its hydrolysis products can be used in conjunctive therapy with other known anti-angiogenic chemotherapeutic or antineoplastic agents (e.g., vinca alkaloids, antibiotics, antimetabolites, platinum coordination complexes, etc.). For instance, the compounds of formula I or its preferred embodiment Oleuropein or its hydrolysis products can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known anti-angiogenic chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be infused are used in the formulation. Such penetrants are generally known in the art.

For oral administration, the compounds of formula I or its preferred embodiment Oleuropein or its hydrolysis products can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Alternatively, other delivery systems for hydrophobic pharmaceutical compounds may be employed. Liposomes and emulsions are well known examples of delivery vehicles or carriers for hydrophobic drugs.

In addition, targeting of a marker on abnormal tumor vasculature can be employed. The targeting moiety when coupled to a toxic drug or radioisotope will act to concentrate the drug where it is needed. Ligands for tumor-associated vessel markers can also be used. For example, a cell adhesion molecule that binds to a tumor vascular element surface marker can be employed. Liposomes and other drug delivery systems can also be used, especially if their surface contains a ligand to direct the carrier preferentially to the tumor vasculature. Liposomes offer the added advantage of shielding the drug from most normal tissues, thereby reducing the inherent toxicity of many compounds. When coated with polyethylene glycol (PEG) (i.e., stealth liposomes) to minimize uptake by phagocytes and with a tumor vasculature-specific targeting moiety, liposomes offer longer plasma half-lives, lower non-target tissue toxicity, and increased efficacy over non-targeted drug. Other targeting strategies include, but are not limited to, ADEPT (antibody-directed enzyme prodrug therapy), GDEPT (gene-directed EPT) and VDEPT (virus-directed EPT). In ADEPT, the targeting of an inactive prodrug to a tumor mass is effected by an antibody against a tumor-associated marker. The enzyme milieu in or about the tumor transforms the prodrug into an active toxic agent that then acts on the tumor tissue. Similarly, differential gene expression or viral targeting at the tumor site is used to activate a prodrug into its active, toxic form in GDEPT and VDEPT, respectively. Other strategies include targeting differentially expressed genes, enzymes or surface markers that appear on tumor-associated vasculature, to effect control of tumor growth. Using the foregoing methods, the compounds of formula I or its preferred embodiment Oleuropein or its hydrolysis products can be targeted to the tumor vasculature to effect control of tumor progression or to other sites of interest (e.g., endothelial cells).

Certain organic solvents such as dimethylsulfoxide also may be employed. Additionally, the compounds may be delivered using a sustained-release system, such as semi-permeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

Presently, it is contemplated that therapeutically effective amounts of the compounds utilized in the practice of the present invention can comprise anywhere between approximately 0.030 g to 20.000 g of such compound per kilogram mass of body weight of the subject.

F. EXAMPLES

The invention will be described in greater detail by way of specific examples. The following example is offered for illustrative purposes, and is not intended to limit the invention in any manner. Those of skill in the art will readily recognize a variety of noncritical parameters which can be changed or modified to yield essentially the same results.

Example 1

This example illustrates the anti-angiogenic properties of Oleuropein in the chick chorioallantoic membrane assay (CAM). The endpoint of the CAM assay was a quantitative determination of the number of branch points and ends of blood vessels in the chorioallantoic membrane. Such a quantitation would illustrate the complexity of the blood vasculature in the developing chorioallantoic membrane. The decrease in the complexity of the blood vasculature of the chorioallantoic membrane as a result of the application of Oleuropein indicates its anti-angiogenic properties.

A. Approach

The CAM in the developing chick embryo is an excellent in vivo system for studying angiogenesis, because there is ongoing new blood vessel growth. The CAM assay involves the monetering of the blood vasculature of the developing chorioallantoic membrane of live chick embryos. Various CAM assay approaches have been developed. These include the culturing of live chick embryos in Petri dishes under special sterile conditions. Another approach has been to cut a window in the shell of fertilized eggs and directly apply the compound to be studied in the window using a filter paper. We used a modified approach to the CAM assay, which includes a less invasive method for introducing the compound Oleuropein. Fertilized chicken eggs where candled on the third day of development. The blood vasculature and the yolk were identified. A small 1 mm hole was made in the shell. A small gauge needle carrying 0.4 ml of Oleuropein diluted in saline/water was injected directly into the yolk sac. The hole was taped and the eggs were returned to the incubator for further development. After 3 days the eggs were removed and cracked in a white dish and the chorioallantoic membrane was photographed. Control eggs were injected with saline/water.

B. Materials

Fertilized eggs were supplied by Country Farm Eggs, Los Angeles, Calif. PBS was obtained from Sigma-Aldrich Chemical Co., St. Louis, Mo. Oleuropein was obtained from Indofine chemical company, Inc., Somerville, N.J. Needles and lancets were obtained from Express Pharmacy Services, Pittsburgh, Pa. Disecting microscope was purchased from Microscope World, Encinitas, Calif. A table top TX7 incubator was obtained from Lyons Electric Company Inc. Chula Vista, Calif. A Kodak MDS-100 camera was purchased from the Eastman Kodak company, New Haven, Conn.

C. Development of the CAM for Measuring Angiogenesis Inhibition

Fresh fertile eggs were incubated for three days in a standard egg incubator. Temperature and humidity were kept constant at 100° F. and 65% respectively. On Day 3, eggs were candled using a police flash light. Embryo and yolk were identified. The surface of the shell was cleaned with an alcohol swab. The egg shell was pierced with a lancet making a 1 millimeter hole. A needle was used to withdraw 0.5 ml of yolk. A 0.5 ml injection was administered directly into the yolk sack. Previous experiments showed that injection of ink, with same consistency used in our experimental and control injections, diffused into the yolk sac within seconds of injection. Experimental eggs were injected with a 0.1% and 1.0% concentration of Oleuropein. Control eggs were injected with an equivalent amount of water. After injection the hole was covered with a small piece of scotch tape and the eggs were returned to the incubator for further development. On day 3 post injection the eggs were removed from the incubator and candled. They were cracked gently using a butter knife over a white dish. Embryo and CAM were carefully layed out for observation and photography. The heart beat of the embryo was recorded using a live feed video with a Kodak mds-100 camera attached to a stereo microscope. Embryo morphology was noted and embryos were photographed using a canon camera. The blood vasculature in the CAM was also photographed using the Kodak mds 100 camera mounted on a stereo microscope.

E. Results

Table 1 shows the anti-angiogenic effect of Oleuropein on the chick embryo CAM. The results summerize two different experiments with a total of 17 eggs with 102 fields photographed for the analysis. Oleuropein showed statistically significant inhibitory effects on CAM angiogenesis. A 0.93 $\mu$mol/egg injection of Oleuropein caused the inhibition of blood vessel growth by 73% compared to control. A 9.3 $\mu$mol/egg injection of Oleuropein caused the inhibition of blood vessel growth by 84% compared to control. The results from these two experiments suggest that Oleuropein is a potent angiogenic inhibitor. It is to be understood that the above used concentrations are intended to be illustrative and not restrictive.

TABLE 1

INHIBITORY EFFECT OF OLEUROPEIN ON ANGEOGENESIS IN THE CHICK EMRYO ASSAY

| Compounds | Dose ($\mu$mole/egg) | Number Nodes + Ends (mean ± S.E.) | % Inhibition |
| --- | --- | --- | --- |
| Oleuropein | 9.3 | 44 ± 5.3[a] | 84 |
|  | 0.93 | 72 ± 11[b] | 73 |
| Control | — | 271 ± 25 | — |

[a]Significantly lower than control, P < 0.0001
[b]Significantly lower than control, P < 0.0001

An example of the inhibition of angiogenesis by Oleuropein is clearly illustrated by representative photographs taken of the CAM at the conclusion of the experiment. FIG. 1 shows representative photographs of the CAM of eggs treated with a 9.3 $\mu$mol/egg of Oleuropien. In these CAMs the number of blood vessels is greatly diminished and branching is less complex than in controls, which are displayed in FIG. 3. Not only are the capillary beds obliterated but midsize and even large vessels have broken down or are in the process of breaking down. Even a 0.93 $\mu$mol/egg of Oleuropien potently inhibited CAM vasculature (FIG. 2) as compared with extensive blood vessel networks in control CAMs (FIG. 3). A closer look at the capillary bed, where most gas exchange takes place near the edge of the CAM, illustrates a disappearance of the extensive capillary networks in the Oleuropein treated eggs as compared with control eggs (FIG. 4).

Also observed in the CAM assay as a result of Oleuropein treatment was the shrinkage of the CAM and embryo (FIG. 5). The CAM assay has been traditionally used to assess the anti-angiogenic property of various compounds. These compounds have been customarily applied to a small window opened at the surface of egg and did not effect the CAM or embryo as a whole. In this example we have used a modification of the CAM assay to assess the effect of Oleuropein on the whole CAM and subsequently on the size of the embryo. In animal development the embryo is undergoing rapid cell divisions as well as cellular differentiation and morphogenesis. An anology could be drawn between the rapid cell division and growth in the developing chick embryo with the rapid cell division and growth of tumor cells. Growth in both examples depends on blood supply. The chick embryo needs a highly vascularized CAM to sustain cell division and growth. In much the same way, a tumor needs to become highly vascularized to sustain cell division and growth. Limiting the blood supply will shrink the embryo and by inference the same could be said of tumors. In this modified CAM assay Oleuropein significantly diminished blood vessel growth and a subsequent shrinkage of the embryo was observed (FIG. 5). The illustrative example shown in FIG. 5 indicates that there was a direct correlation between CAM size and embryo size. The Oleuropein treated CAM was about 50% smaller in diameter than the control CAM. The Oleuropein treated embryos were correspondingly smaller by about 60% the size of the untreated control embryos. The higher dose of Oleuropein although dramatically effecting both CAM size and embryo size did not effect embryo viability.

Example 2

This example illustrates the anti-angiogenic properties of the olive leaf extract in the chick chorioallantoic membrane assay (CAM). The endpoint of the CAM assay was a direct visualization of the number of branch points and ends of blood vessels in the chorioallantoic membrane. Such visualization would illustrate the complexity of the blood vasculature in the developing chorioallantoic membrane. The decrease in the complexity of the blood vasculature of the chorioallantoic membrane as a result of the application of the olive leaf extract indicates its anti-angiogenic properties.

A. Approach

As described in example 1, the CAM assay was used to assess the anti-angiogenic properties of the olive leaf extract.

B. Materials

Fertilized eggs were supplied by Country Farm Eggs, Los Angeles, Calif. PBS was obtained from Sigma-Aldrich Chemical Co., St. Louis, Mo. Olive leaf extract was obtained from the olive leaf. Needles and lancets were obtained from Express Pharmacy Services, Pittsburgh, Pa. Dissecting microscope was purchased from Microscope World, Encinitas, Calif. A tabletop TX incubator was obtained from Lyons Electric Company Inc. Chula Vista, Calif. A Kodak MDS-100 camera was purchased from the Eastman Kodak Company, New Haven, Conn.

C. Development of the CAM for Measuring Angiogenesis Inhibition

Fresh fertile eggs were incubated for three days in a standard egg incubator. Temperature and humidity were kept constant at 100° F. and 65% respectively. On Day 3, eggs were candled using a police flashlight. Embryo and yolk were identified. The surface of the shell was cleaned with an alcohol swab. The eggshell was pierced with a lancet making a 1-millimeter hole. A needle was used to withdraw 0.5 ml of yolk. A 0.5 ml injection was administered directly into the yolk sack. Previous experiments showed that injection of ink, with same consistency used in our experimental and control injections, diffused into the yolk sac within seconds of injection. Experimental eggs were injected with water containing olive leaf extract. Control eggs were injected with an equivalent amount of water. Ten mlliliters of Boiling water was added to a half-teaspoon of crushed dried olive leaves and extraction was carried out for 2 hours before use of the extract in the experiment. After injection the hole was covered with a small piece of scotch tape and the eggs were returned to the incubator for further development. On day 4-post injection the eggs were removed from the incubator and were cracked gently using a butter knife over a white dish. Embryo and CAM were carefully layed out for observation and photography. The heartbeat of the embryo was recorded using a live feed video with a Kodak mds-100 camera attached to a stereomicroscope. Embryo morphology was noted and embryos were photographed using a canon camera. The blood vasculature in the CAM was also photographed using the Kodak mds 100 camera mounted on a stereomicroscope.

C. Results

The results from three experiments suggest that the olive leaf extract is a potent angiogenic inhibitor. It is to be understood that the above used concentrations are intended to be illustrative and not restrictive. An example of the inhibition of angiogenesis by olive leaf extract is clearly illustrated by representative photographs taken of the CAM at the conclusion of the experiments. FIG. 1 shows representative photographs of the CAM of control eggs (FIGS. 6a, b, and c) and eggs treated with olive leaf extract (FIGS. 6d, e, and f). In the treated CAMs the number of blood vessels is greatly diminished and branching is less complex than in controls.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

Example 3

This example illustrates the anti-angiogenic properties of Oleuropein in the adult mouse ear model. The endpoint of the adult mouse ear model assay was a direct visualization of the number of branch points and ends of blood vessels. Such visualization would illustrate the complexity of the blood vasculature in the adult mouse ear. The decrease in the complexity of the induced blood vasculature of the adult mouse ear as a result of the application of Oleuropein would indicate its anti-angiogenic properties.

A. Approach

In the previous model (the CAM in the developing chick embryo), although an excellent in vivo system for studying angiogenesis, because there is ongoing new blood vessel growth in the growing embryo, we tested another model in assessing whether Oleuropein can inhibit induced blood vessel growth in an adult mammal. The model we chose to use was the adult mouse ear. The mouse ear is vascularized and is thin enough to be directly visualized by a light microscope. If a stimulus is applied to the adult mouse ear existing blood vessels are capable of sprouting new ones (angiogenesis). Using this model anti-angiogenic compounds can be tested for their effects. We applied a sodium hydroxide burn, which stimulated the existing blood vessels in the adult mouse ear to sprout new blood vessels. Prior to the application of the sodium hydroxide burn the experimental mice were intraperitoneally injected with phosphate buffered saline containing Oleuropein. Control mice were intraperitoneally injected with phosphate buffered saline alone. The sodium hydroxide burn was applied to the ears of both groups. A third group of mice were not injected and not burned. This third group of mice shows the status of the uninduced blood vessels in the adult mouse ear. The adult mouse ear assay involved the monitoring of the blood vasculature of the ear in the adult mouse three days after the application of the sodium hydroxide burn.

B. Materials

Mice were bred by inventors in a clean and healthy environment. PBS was obtained from Sigma-Aldrich Chemical Co.; St. Louis, Mo. Oleuropein was obtained from Indofine chemical company, Inc., Somerville, N.J. Sodium hydroxide was obtained from Sammy's Camera in Los Angeles. Needles and Nair were obtained from Thrifty's drugs in Los Angeles Calif. Dissecting microscope was purchased from Microscope World, Encinitas, Calif. A Kodak MDS-100 camera was purchased from the Eastman Kodak Company, New Haven, Conn.

C. Development of the Adult Mouse Ear Model for Measuring Angiogenesis Inhibition Mice were used when they were fully grown at 2–3 months. Experimental mice were injected intraperitoneally with 0.25 ml of phosphate buffered saline containing 0.025 grams of Oleuropein. Control mice were injected with 0.25 ml phosphate buffered saline alone. The experimental and control groups were injected intraperitoneally once a day for three days prior to the sodium hydroxide burn. On the fourth day a cotton q-tip moistened with a 2% sodium hydroxide solution was applied for a total time of one minute to the ears of both groups of mice. The ears were subsequently washed with copious amounts of water. The mice were returned to the cages for another 3 days, during which time they were given intraperitoneal injections once a day. On the $4^{th}$ day the mice were humanly killed by cervical dislocation. The ears were treated with Nair to remove excess hair and the blood vasculature was photographed using a digital MDS-100 camera attached to a stereomicroscope.

E. Results

A total of five control (burned) mice, five experimental (burned and Oleuropein treated), and five control (unburned and untreated) mice were used in the experiment above with a total of 30 ears. The results from the above experiment showed that Oleuropein is a potent angiogenic inhibitor. An example of the inhibition of angiogenesis by Oleuropein is clearly illustrated by representative photographs taken of the mouse ears at the conclusion of the experiment. FIG. 7 shows a comparison of the ears of all three groups of mice. The ears of mice that have not been burned or treated in any way clearly show some vascularization (FIG. 7a). The ears of mice in the control group that have been burned with sodium hydroxide show an increased amount of vascularization, indicating that we were successful in inducing blood vessel growth (FIG. 7b). A striking example of induced blood vessel growth can be seen in FIG. 7c, where new vessels can be seen sprouting from an existing blood vessel and traveling towards the area of the burn. The potent anti-angiogenic effect of Oleuropein is shown in FIG. 7d. In this figure the ears were treated with sodium hydroxide and the mice also received daily doses of Oleuropein. It can be seen that Oleuropein potently inhibited existing blood vessels from sprouting. The burn area is in fact devoid of blood vessels. This was a consistent result with all the mice that were given daily injections of Oleuropein.

It is to be understood that the above description and the amount of Oleuropein used are intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

Example 4

This example illustrates the anti-angiogenic properties of olive leaf extract in the adult mouse ear model. The endpoint of the adult mouse ear model assay was a direct visualization of the number of branch points and ends of blood vessels. Such visualization would illustrate the complexity of the blood vasculature in the adult mouse ear. The decrease in the complexity of the induced blood vasculature of the adult mouse ear as a result of the application of olive leaf extract would indicate its anti-angiogenic properties.

A. Approach

As described in example 3, the adult mouse ear model was used to assess the anti-angiogenic properties of the olive leaf extract.

B. Materials

Mice were bred by inventors in a clean and healthy environment. PBS was obtained from Sigma-Aldrich Chemical Co., St. Louis, Mo. Olive leaf extract was obtained from the olive leaf. Sodium hydroxide was obtained from Sammy's Camera in Los Angeles. Needles and Nair were obtained from Thrifty's drugs in Los Angeles Calif. Dissecting microscope was purchased from Microscope World, Encinitas, Calif. A Kodak MDS-100 camera was purchased from the Eastman Kodak Company, New Haven, CT.

C. Development of the Adult Mouse Ear Model for Measuring Angiogenesis Inhibition Mice were used when they were fully grown at 2–3 months. Experimental mice were injected intraperitoneally with 0.25 ml of phosphate buffered saline containing olive leaf extract. The olive leaf extract was prepared by grinding dried olive leaves in a coffee grinder until the leaves were in a powdered form. Ten milliliters of packed powdered leaves were mixed with 45 milliliters of hot water. Phosphate buffered saline was added to the mixture. The experimental and control groups were injected intraperitoneally once a day for three days prior to the sodium hydroxide burn. Each mouse received a 0.25ml injection. The experimental group received a phosphate buffered saline injection containing the olive leaf extract. The control group received a phosphate buffered saline injection alone. On the fourth day a cotton q-tip moistened with a 2% sodium hydroxide solution was applied for a total time of one minute to the ears of both groups of mice. The ears were subsequently washed with copious amounts of water. The mice were returned to the cages for another 3 days, during which time they were given intraperitoneal injections once a day. On the $4^{th}$ day the mice were humanly killed by cervical dislocation. The ears were treated with Nair to remove excess hair and the blood vasculature was photographed using a digital MDS-100 camera attached to a stereomicroscope.

E. Results

A total of seven control mice and seven experimental mice were used in the experiment above with a total of 28 ears. The results from the above experiment show that the olive leaf extract is a potent angiogenic inhibitor. An example of the inhibition of angiogenesis by olive leaf extract is clearly illustrated by representative photographs taken of the mouse ears at the conclusion of the experiment. FIG. 8 shows representative photographs of eight independent ears from control mice (FIGS. 8a, b, c, and d) and mice treated with the olive leaf extract (FIGS. 8e, f, g, and h). The ears of control mice were highly vascularized indicating an induction of new blood vessel growth. Mice treated with the olive leaf extract had diminished vascularization, indicating the potent effect of the olive leaf extract in inhibiting new blood vessel growth.

It is to be understood that the above used amounts of olive leaf extract are intended to be illustrative and not restrictive. It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. A method for treating a medical condition which involves angiogenesis in a subject, the method comprising administering to a subject in need of such treatment a therapeutically effective amount of a pharmaceutical composition having anti-angiogenic activity which contains as an active ingredient a therapeutically effective quantity of a compound of the formula:

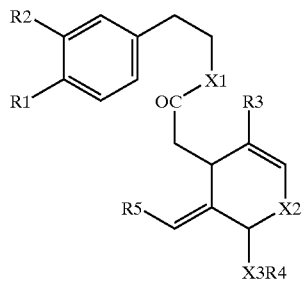

wherein R1 and R2 are hydroxyl functional groups:
R3 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $COOCH_3$;
X1–X3 are functional groups selected from the group consisting of oxygen, sulfur, —$CH_2$—, or carboxy;
R4 is a functional group selected from the group consisting of hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen $NO_2$, $NH_3$, carbohydrate, amino acid, nucleotide and lipid; and
R5 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $CH_3$.

2. The method of claim 1 wherein the pharmaceutical composition includes the pharmaceutically acceptable carrier or diluent.

3. A method of inhibiting the vascularization of endothelial cells comprising contacting said cells with a pharmaceutical composition in an amount sufficient to inhibit the vascularization thereof which contains an effective amount of a compound of the formula:

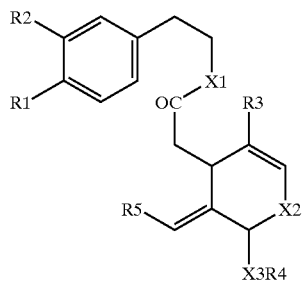

wherein R1 and R2 are hydroxyl functional groups:
R3 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $COOCH_3$,
X1–X3 are functional groups selected from the group consisting of oxygen, sulfur, —$CH_2$—, or carboxy;
R4 is a functional group selected from the group consisting of hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen $NO_2$, $NH_3$, carbohydrate, amino acid, nucleotide, and lipid; and
R5 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $CH_3$.

4. The method of claim 3 wherein the pharmaceutical composition includes a pharmaceutically acceptable carrier or diluent.

5. The method of claim 3 wherein said inhibition of the vascularization of the endothelial cells is conducted in vivo.

6. The method of claim 3 wherein said inhibition of the the vascularization of said endothelial cells is conducted in vitro.

7. A method for treating a medical condition in which involves angiogensis in a subject, which comprises administering to a subject in need of such treatment a therapeutic or effective amount of a pharmaceutical composition having anti-angiogenic activity which contains as an active ingredient at least one composition produced by the hydrolysis of a compound of the formula:

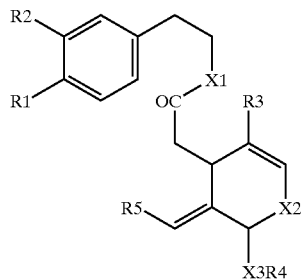

wherein R1 and R2 are hydroxyl functional groups:
R3 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $COOCH_3$;
X1–X3 are functional groups selected from the group consisting of oxygen, sulfur, —$CH_2$—, or carboxy;
R4 is a functional group selected from the group consisting of hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen $NO_2$, $NH_3$, carbohydrate, amino acid, nucleotide and lipid; and
R5 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $CH_3$.

8. A method of enhibiting the vascularization of endothelial cells comprising contacting said cells with a pharmaceutical composition in an amount sufficient to inhibit the vascularization thereof which contains as an effective amount a compound selected from the group consisting of at one composition produced by the hydrolysis of a compound of the formula:

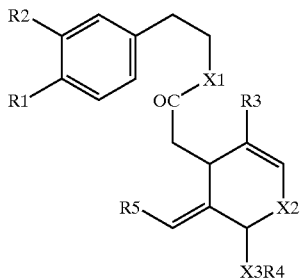

wherein R1 and R2 are hydroxyl functional groups:
  R3 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $COOCH_3$;
  X1–X3 are functional groups selected from the group consisting of oxygen, sulfur, —$CH_2$—, or carboxy;
  R4 is a functional group selected from the group consisting of hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen $NO_2$, $NH_3$, carbohydrate, amino acid, nucleotide and lipid; and
  R5 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $CH_3$.

9. The method of claim 1 wherein said composition comprises the formula:

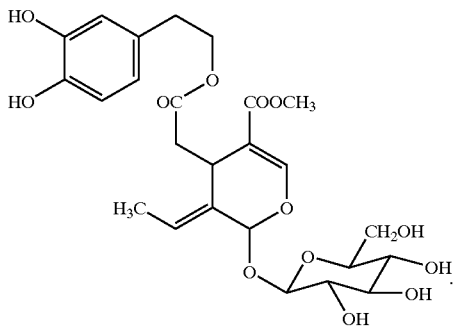

10. The method of claim 3 wherein said composition comprises the formula:

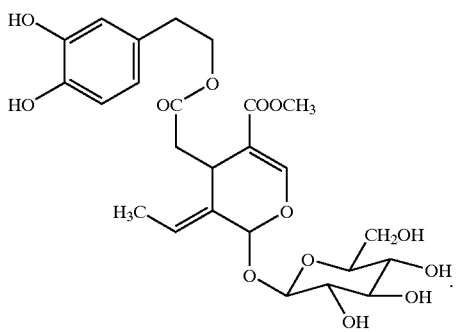

11. A method of treating cancer in a mammal in need of such treatment which is comprised of administering to said patient a therapeutically effective amount of a compound having the structure:

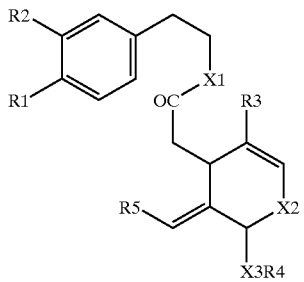

wherein R1 and R2 are hydroxyl functional groups:
  R3 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$ and $COOCH_3$,
  X1–X3 are functional groupsmne selected from the group consisting of oxygen, sulfur, —$CH_2$—, or carboxy;
  R4 is a functional group consisting of hydrogen, $C_1$–$C_6$-alkoxy, glucose, B-D-glucopyranose, $C_1$–$C_6$-alkyl, $C_2$–$C_6$-alkenyl, $C_2$–$C_6$-alkynyl, aryl, hydroxyl, halogen $NO_2$, $NH_3$, carbohydrate, amino acid, nucleotide, and lipid; and
  R5 is a functional group selected from the group consisting of hydrogen, $C_1$–$C_6$-alkyl, $C_2$–$C_6$-alkenyl, $C_2$–$C_6$-alkynyl, aryl, hydroxyl, $C_1$–$C_6$-alkoxy, halogen, $NO_2$, $NH_3$, and $CH_3$; or a pharmaceutically acceptable salt, prodrug or hydrate thereof.

12. The method of treating cancer in accordance with claim 11 wherein said cancer is selected from cancers of the lung, larynx, colon, rectum, pancreas, stomach, liver, lung, breast, skin, prostate, ovary, cervix, uterus, and bladder.

13. The method of treating cancer in accordance with claim 11, wherein the cancer is selected from lymphoma, leukemia, glioblastoma, sarcoma and retinoblastoma.

14. The method of claim 1 wherein the condition is an ocular disease.

15. The method of claim 14 wherein the ocular disease comprises a disease associated with corneal neovascularization selected from the group consisting of diabetic retinopathy, retinopathy of prematurity, corneal graft rejection, neovascular glaucoma and retrolental fibroplasias, epidemic keratoconjunctivitis, vitamin A deficiency, contact lense overwear, atopic keratitis, superior limbic keratitis, pterygium keratitis sicca, sjogrens, acne rosacea, phylectenulosis, syphilis, mycobacteria infections, lipid degeneration, chemical burns, bacterial ulcers, fungal ulcers, herpes simplex infections, herpes zoster infections, protozoan infections, Kaposi sarcoma, Mooren ulcer, terrien's marginal degeneration, marginal keratolysis, trauma, systemic lupus, polyarteritis, Wegeners sarcoidosis, scleritis, Steven's Johnson disease, peraphigoid radial caratotomy and corneal graft rejection.

16. The method of claim 14, wherein such ocular disease is a disease associated with a retinal/choroidal neovascularization selected from the group consisting of diabetic retinopathy, macular degeneration, sickle cell anemia, sarcoid, syphilis, pseudoxanthoma elasticurn, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

17. The method of claim 14, wherein said ocular disease is selected from the group consisting of rubeosis and proliferative atrial retinopathy.

18. The method of claim 1, wherein said condition comprises a disease associated with chronic inflammation selected from the group consisting of inflammatory bowel disease, psorsasis, sarcoidosis, and rheumatoid arthritis.

19. The method of claim 18, wherein said inflammatory bowel disease selected from the group consisting of Crohn's disease and ulcerative colitis.

20. The method of claim 1 wherein said compound is administered via a route selected from the group consisting of oral, buccal, rectal, parenteral, intraperitoneal, intradermal, transdermal, and intracheal.

21. The method of claim 1 wherein said composition is formulated as a tablet or elixer for oral administration.

22. The method of claim 1 wherein said composition is administered via a route selected from the group consisting of intramuscular or intravenous administration.

23. The method of claim 1 wherein said composition is administered via inhalation.

24. The method of claim 11 wherein said compound is administered via a route selected from the group consisting of oral, buccal, rectal, parenteral, intraperitoneal, intradermal, transdermal, and intracheal.

25. The method of claim 11 wherein said composition is formulated as a tablet or elixer for oral administration.

26. The method of claim 11 wherein said composition is administered via a route selected from the group consisting of intramuscular or intravenous administration.

27. The method of claim 11 wherein said composition is administered via inhalation.

28. The method of treating cancer in accordance with claim 11 wherein said composition comprises the formula:

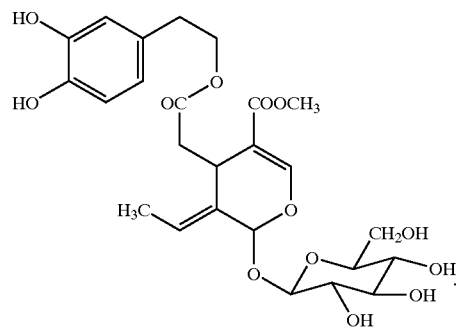

29. The method of claim 7 when said at least one composition is selected from the group consisting of oleuropein aglycone, elenolic acid, beta-3,4,-dihydroxyphenyethyl alcohol and methyl-o-methyl elenolate.

30. The method of claim 8 wherein said at least one composition is selected from the and methyl-o-methyl elenolate.

* * * * *